United States Patent
Sawatzki et al.

(12)

(10) Patent No.: US 6,656,903 B1
(45) Date of Patent: Dec. 2, 2003

(54) BABY FOOD STIMULATING GROWTH OF THE THYMUS

(75) Inventors: Gunther Sawatzki, Munzenberg (DE); Gunther Bohm, Echzell (DE); Gilda Georgi, Friedrichsdorf (DE)

(73) Assignee: N. V. Nutricia, Zoetermeer (NL)

( * ) Notice: Subject to any disclaimer, the term of this patent is extended or adjusted under 35 U.S.C. 154(b) by 0 days.

(21) Appl. No.: 09/856,483

(22) PCT Filed: Dec. 7, 1999

(86) PCT No.: PCT/EP99/09565

§ 371 (c)(1),
(2), (4) Date: Jul. 16, 2001

(87) PCT Pub. No.: WO00/33662

PCT Pub. Date: Jun. 15, 2000

(30) Foreign Application Priority Data

Dec. 9, 1998  (DE) .......................................... 198 56 789

(51) Int. Cl.[7] .............................. A23L 1/00; A23I 3/00; A23D 7/00
(52) U.S. Cl. .......................... 514/2; 426/655; 426/656; 426/658; 426/531; 426/567; 426/801; 426/23; 426/74; 426/601
(58) Field of Search ................................. 426/531, 567, 426/23, 74, 601, 656, 655, 658, 801; 435/114; 514/2

(56) References Cited

U.S. PATENT DOCUMENTS 5,550,146 A  * 8/1996 Acosta et al. ................ 514/400
5,591,479 A  * 1/1997 Ponroy ........................ 426/662

FOREIGN PATENT DOCUMENTS

| EP | 0 048 473 A | 3/1982 |
|---|---|---|
| EP | 0 891 719 A | 1/1999 |
| GB | 2 323 531 A | 9/1998 |
| WO | 94/01006 A | 1/1994 |

OTHER PUBLICATIONS

Golden, M. H. N. (Lacent (1997) "Effect of zinc on thymus of recently malnorished children" vol. 2, issue Nov. 19, pp. 1057–1059.*
Hasselbalch, H. et al (1996) "Decreased thymus size in formula–fed infant compared with breastfed infant" Acta Paediatr. vol. 85, pp. 1029–1032.*
Decsi, T. et al (1998) "Plasma amino acid concentrations, indexes of protein metabolism and growth in health, full–term infants fed partially hydrolyzed infant formula" J. Pediatric Gastroenterol. Nutr. vol. 27, pp. 12–16.*
Daly, J. M. et al (1990) "Effect of dietary protein and amino acids on immune function" Crit. Care Medicine, vol. 18, pp. S86 S93.*

* cited by examiner

*Primary Examiner*—Karen Cochrane Carlson
*Assistant Examiner*—Samuel W. Liu
(74) *Attorney, Agent, or Firm*—Bacon & Thomas, PLLC

(57) ABSTRACT

A thymus growth stimulating baby food is provided, substantially composed of a fat component, as well as a carbohydrate component and a protein component of animal or vegetable or animal and vegetable but not human origin, whereby the protein component is composed of intact proteins, hydrolyzed proteins, peptides or the constituents thereof, or of amino acids or a mixture thereof not bound to peptides or proteins. This type of baby food is characterized in that the total amount of arginine is at least 3.7 g per 100 g of the amino acids present in toto, and that it contains zinc (calculated as elementary zinc) in an amount of at least 40 mg per 100 g of the amino acids present in toto.

23 Claims, No Drawings

BABY FOOD STIMULATING GROWTH OF THE THYMUS

The invention relates to a thymus growth stimulating baby food, a protein component for preparing such a baby food, and the use of this protein component for stimulating the thymus growth of babies.

At the time of birth, the human immunosystem is still relatively immature. The thymus thereby plays a very important role for the maturation particularly of the T-lymphocytes. Immature T-lymphocytes from the bone marrow are differentiated in the thymus from immunocompetent T-lymphocytes. In particular, the thymus is active during the first months of life, later on, the organ recedes.

Regulation of the thymus function ensues by means of a very complex and a highly species-specific hormonal regulation. Many questions in this respect are still unanswered.

It could be shown in more recent researches that the thymus size of the human baby also depends on food. Children who are nourished with mother milk exhibit a significantly larger thymus than children who are fed with formula food. Moreover, it is known that babies nourished with mother milk respond to vaccinations during the first year of life with a higher antibody production than it is the case with children fed with formula food. Up to now, the cause for these differences cannot yet be derived from the tests conducted on humans.

The object of the present invention is to show ways by means of which the thymus growth can be stimulated so that it corresponds approximately to that of a nourishment with mother milk.

This task is solved by the teaching of the claims.

Surprisingly, it was namely found that the use of baby foods rich in arginine with a simultaneous supplementation of zinc contributes to stimulating the thymus growth and the thymus function during the nursing period. This leads, for example, to an increase of the thymus weight of formula-fed babies, whereby the difference to breast-fed babies can be reduced or even balanced.

So as to achieve the desired effect, the infantile organism must be supplied with arginine, as well as with zinc in a sufficient amount.

So as to reach this target, arginine and zinc can be added to the usual baby foods. The total amount of arginine contained in the baby food must thereby be at least 3.7 g of arginine/100 g of amino acids. At the same time, such an amount of zinc must be added that a zinc content of at least 40 mg per 100 g of the amino acids present in toto is reached. In the case of bovine milk proteins, the supplemented amount of arginine should for this purpose be at least 0.5 g/100 g of food protein.

The desired amount of arginine and zinc in the baby food can be obtained by the addition of particularly arginine-rich proteins or peptides, or by the addition of arginine not bound to proteins or peptides together with zinc compounds such as zinc salts, or by arginine-zinc complexes. These arginine-rich proteins and peptides include, for example, leguminose proteins such as soybean proteins and pea proteins and the peptides thereof. Zinc acetate, zinc gluconate, zinc chloride, zinc lactate, zinc sulfate, zinc citrate and zinc oxide count among the zinc compounds. With the arginine not bound to proteins or peptides, appropriately the L configuration is concerned.

The core of the present invention therewith consists in administering an arginine-enriched and zinc-enriched or an arginine-rich and zinc-rich food to a baby for achieving its normal thymus growth.

Appropriately, arginine and zinc are incorporated for this purpose in a baby food, and in particular in the protein component of the baby food concerned.

It is, however, also possible to administer arginine-rich proteins or peptides or arginine not bound to proteins and peptides together with zinc in addition to a conventional baby food or formula food. Thus, for example, the baby organism can be supplied with free arginine and zinc in an appropriate form, for example, by incorporating this additive of arginine and zinc in a conventional baby food during its preparation, or by administering this additive to the child separately from the baby milk food, but in a relatively short space of time therefrom. It is, however, preferred to incorporate arginine and zinc a priori into the baby food to be fed.

The inventive baby food or formula food contains therewith, apart from a usual fat component and a usual carbohydrate component, also a protein component with an arginine content of at least 3.7 g per 100 g of the amino acids present in toto. As protein components, usual intact proteins, hydrolyzed proteins, peptides or constituents thereof or one or more L amino acid(s) not bound to peptides or proteins can thereby be used. Appropriately, the protein component represents a mixture of one or more of these components.

For the preparation of the protein component, all usual proteins or their members or fractions, which have been hitherto used for the preparation of formula food and baby food, can therewith be used. The types of the initial components is in this case not decisive, but rather the content of arginine.

Such proteins and peptides can also be admixed with one or more amino acid(s) not bound to peptides or proteins. Among these amino acids count not only the free amino acids but also the salts, esters and other usual derivatives thereof.

One field of application of the present invention concerns, for example, baby foods on a bovine milk basis. Usual baby foods of this kind contain exclusively proteins, peptides or the hydrolysates thereof originating from bovine milk. So as to obtain the desired arginine content, the mentioned arginine-rich proteins, peptides and hydrolysates thereof can be added, such as, for example, soybean proteins or soybean peptides. In addition or instead, arginine which is not bound to proteins or peptides can be added. The desired zinc content can be achieved by adding the mentioned zinc compounds.

Within the scope of the present documents, formula food is understood as an artificially produced baby food or infant food including baby milk food, etc., which are prepared with the use of animal and/or vegetable initial substances including, if the case may be, microbic initial substances, whereby these initial substances, however, are not of human origin. Thus, all initial substances known and/or suitable for the preparation of such artificial formula foods can be used. Only the arginine and zinc content is decisive.

It is known that 100 g of protein or peptide contain more than 100 g of amino acids, since upon decomposition of the amino acid sequence forming said peptide or protein, water is incorporated, so that the sum of the amino acids generated from one protein or peptide is larger than 100 g.

So as to take this circumstance into account, the gram indications relative to the arginine amount and also relative to the amino acids present in toto, refer to the molecular weight of the free amino acids expressed in grams, reduced by the molecular weight of water. This applies therewith independent of the form in which the respective amino acids are bound (e.g. peptides, proteins) or not bound (e.g. free amino acids, salts, esters and other usual derivatives). The calculation therewith is carried out on the basis of the molecular weights of the respective amino acids reduced by the water portion. The same applies to the indication that, according to the invention, at least 40 mg of zinc per 100 g of the amino acids present in toto are used. In this case, as well, the molecular weights of the amino acids enter into the calculations without the water portion. The indicated zinc amount is thereby given as elementary zinc, independent of the form of the zinc (for example zinc salt) used.

When reference is made within the scope of the present invention as to that the total amount of arginine is at least 3.7 g per 100 g of the amino acids present in toto, then all values above 3.7 g are therewith disclosed, as well. Thus, for example, a total arginine amount of 3.8 g, 3.9 g, 4.0 g, 4.1 g, 4.2 g, 4.3 g, 4.4 g, 4.5 g, 4.6 g, etc., can also be used according to the invention. The same applies to the amount of zinc, which is at least 40 mg per 100 g of the amino acids present in toto. By this indication, at least all higher integral values for the minimum total amount of zinc are disclosed, for example, 41, 42, 43, 44, 45, 46, 47, 48, 49 and 50 mg, etc. The zinc content is appropriately 40–67 mg.

According to a preferred embodiment, 10 to 80 wt-% of the arginine present in toto is present as arginine not bound to proteins or peptides. Thereby, such as it is stated above, free amino acid arginine or simple salts and derivatives or mixtures thereof can be concerned.

The term "10 to 80 wt-%" embraces all intermediate values and in particular all integral values, and all smaller area values falling in the area between 10 and 80 wt-%. Thus, for example, 10, 11, 12, 13, 14, 15, 16, 17, 18, 19 20, 21, 22, 23, 24, 35, 26, 27, 28, 29, 30, 31, 32, 33, 34, 35, 36, 37, 38, 39, 40, etc., up to 80 wt-% or 10 to 79, 78, 77, 76, 75, 74, 73, 72, 71, 70, 69, 68, 67, 66, 65, 64, 63, 62, 61, 60, etc., wt-% of the arginine present in toto can be present as arginine not bound to proteins or peptides.

It is further preferred to particularly use those proteins and peptides which are rich in arginine.

According to the invention, zinc is preferably used in the form of zinc salts and/or arginine-zinc complexes.

Therewith, all protein raw materials suitable for baby foods and/or baby milks can be supplemented with arginine and/or arginine-rich proteins and arginine-rich peptides and with zinc, and can be used for the preparation of formula foods.

In the following, the invention will be explained in detail by means of examples. describing various protein components or protein mixtures. These protein mixtures can be obtained by simple blending of the indicated components. From these protein mixtures, baby foods or formula food can be prepared in a manner known per se, by blending the protein mixture with the necessary fat component and carbohydrate component in a manner known per se. Furthermore, usual and appropriate additives can be incorporated in the baby foods. Among these count, for example, vitamins, minor nutrient elements, etc.

The arginine-enriched protein mixtures described in the following examples serve as the basis for preparing baby foods which are suitable for stimulating thymus growth.

EXAMPLE 1

Protein mixture on the basis of demineralized sour-whey powder and sodium caseinate. The ratio of whey protein and casein is 60:40.

| | |
|---|---|
| Demineralized sour-whey powder (13.5% of protein) | 90.9 kg |
| Sodium caseinate (89.9% of protein) | 9.1 kg |
| L arginine | 0.4 kg |
| Zinc sulfate monohydrate | 29.9 kg |

The amino acid composition of this arginine-enriched protein mixture can be derived from the following table:

| | g/100 g amino acids |
|---|---|
| Asp | 8.7–9.6 |
| Thr | 4.4–4.9 |
| Ser | 4.5–5.5 |
| Glu | 17.5–19.3 |
| Pro | 6.8–7.6 |
| Gly | 1.6–2.0 |
| Ala | 3.5–4.2 |
| Cys | 1.7–2.1 |
| Val | 4.6–5.6 |
| Met | 2.2–2.7 |
| Ile | 4.3–5.3 |
| Leu | 9.6–10.6 |
| Tyr | 2.9–3.6 |
| Phe | 3.7–4.5 |
| His | 2.4–2.9 |
| Lys | 8.5–9.4 |
| Arg | 4.5–5.5 |
| Trp | 1.4–1.7 |

EXAMPLE 2

Protein mixture on the basis of sweet-whey protein concentrate and sodium caseinate. The ratio of whey protein and casein is 50:50.

| | |
|---|---|
| Sweet-whey protein concentrate (79.8% of protein) | 53.5 kg |
| K-caseinate (91.6% of protein) | 46.5 kg |
| L-Arginine | 2.9 kg |
| Zinc sulfate monohydrate | 126.1 kg |

The amino acid composition of this arginine-enriched protein mixture can be derived from the following table:

| | g/100 g amino acids |
|---|---|
| Asp | 7.8–8.6 |
| Thr | 5.1–5.6 |
| Ser | 4.7–5.7 |
| Glu | 17.7–20.5 |
| Pro | 7.5–8.2 |
| Gly | 1.4–1.8 |
| Ala | 3.1–3.8 |
| Cys | 1.7–2.1 |
| Val | 4.8–5.8 |
| Met | 2.3–2.8 |
| Ile | 4.5–5.5 |
| Leu | 8.8–9.7 |
| Tyr | 3.7–4.4 |
| Phe | 3.6–4.3 |
| His | 2.1–2.5 |
| Lys | 7.8–8.7 |

-continued

| | g/100 g amino acids |
|---|---|
| Arg | 5.6–6.2 |
| Trp | 1.4–1.7 |

What is claimed is:

1. A thymus growth stimulating baby food consisting essentially of a fat component, a carbohydrate component and a protein component of animal or vegetable, or animal and vegetable but not human origin, the protein component comprising intact proteins, hydrolyzed proteins, peptides or the constituents thereof, or amino acids or a mixture thereof; wherein the improvement comprises having a total amount of arginine present in an amount of at least 3.7 g per 100 g of the amino acids present in toto, and zinc (calculated as elementary zinc) present in an amount of at least 40 mg per 100 g of the amino acids present in toto.

2. The baby food according to claim 1, wherein 10 to 80 wt-% of the arginine present in toto is present as arginine not bound to proteins or peptides.

3. The baby food according to claim 1, which contains arginine-rich proteins, arginine-rich protein hydrolysates, arginine-rich peptides or arginine-rich peptide hydrolysates or mixtures thereof.

4. The baby food according to claim 2, which contains arginine-rich proteins, arginine-rich protein hydrolysates, arginine-rich peptides or arginine-rich peptide hydrolysates or mixtures thereof.

5. A baby food according to claim 1, wherein zinc is present in the form of one or more zinc salts or as an arginine-zinc complex or as a mixture thereof.

6. A baby food according to claim 2, wherein zinc is present in the form of one or more zinc salts or as an arginine-zinc complex or as a mixture thereof.

7. A baby food according to claim 3, wherein zinc is present in the form of one or more zinc salts or as an arginine-zinc complex or as a mixture thereof.

8. A baby food according to claim 4, wherein zinc is present in the form of one or more zinc salts or as an arginine-zinc complex or as a mixture thereof.

9. A baby food according to claim 1, which contains as proteins or peptides mixtures of soybean proteins and cow milk proteins or the peptides thereof.

10. A baby food according to claim 2, which contains as proteins or peptides mixtures of soybean proteins and cow milk proteins or the peptides thereof.

11. A baby food according to claim 3, which contains as proteins or peptides mixtures of soybean proteins and cow milk proteins or the peptides thereof.

12. A baby food according to claim 4, which contains as proteins or peptides mixtures of soybean proteins and cow milk proteins or the peptides thereof.

13. A baby food according to claim 5, which contains as proteins or peptides mixtures of soybean proteins and cow milk proteins or the peptides thereof.

14. A baby food according to claim 6, which contains as proteins or peptides mixtures of soybean proteins and cow milk proteins or the peptides thereof.

15. A baby food according to claim 7, which contains as proteins or peptides mixtures of soybean proteins and cow milk proteins or the peptides thereof.

16. A baby food according to claim 8, which contains as proteins or peptides mixtures of soybean proteins and cow milk proteins or the peptides thereof.

17. A baby food according to claim 9, which contains as proteins or peptides mixtures of soybean proteins and cow milk proteins or the peptides thereof.

18. A thymus growth stimulating baby food obtained by raising the arginine and zinc content of a bovine based baby food wherein all of the protein, peptide, and hydrolysate of said protein or said peptide in said bovine based baby food is exclusively of bovine origin; said arginine and zinc content being raised to produce a total arginine content of at least 3.7 g per 100 g of amino acids present in toto and a total zinc content (calculated as elemental zinc) of at least 40 mg per 100 g of amino acids present in toto.

19. A protein component which comprises intact proteins, hydrolyzed proteins, peptides or the constituents thereof, or of amino acids or a mixture thereof wherein the improvement comprises having a total amount of arginine present in an amount of at least 3.7 g per 100 g of the amino acids present in toto, and zinc (calculated as elementary zinc) present in an amount of at least 40 mg per 100 g of the amino acids present in toto.

20. The baby food according to claim 19, wherein 10 to 80 wt-% of the arginine present in toto is present as arginine not bound to proteins or peptides.

21. The baby food according to claim 19, which contains arginine-rich proteins, arginine-rich protein hydrolysates, arginine-rich peptides or arginine-rich peptide hydrolysates or mixtures thereof.

22. The baby food according to claim 20, which contains arginine-rich proteins, arginine-rich protein hydrolysates, arginine-rich peptides or arginine-rich peptide hydrolysates or mixtures thereof.

23. A baby food according to claim 19, wherein zinc is present in the form of one or more zinc salts or as an arginine-zinc complex or as a mixture thereof.

\* \* \* \* \*